United States Patent [19]
Romanelli

[11] Patent Number: 5,849,677
[45] Date of Patent: Dec. 15, 1998

[54] SULFURIZED OLEFIN COMPOSITION AND ITS METHOD OF PREPARATION

[75] Inventor: Michael Gerald Romanelli, Brooklyn, N.Y.

[73] Assignee: Exxon Chemical Patents Inc, Linden, N.J.

[21] Appl. No.: 579,323

[22] Filed: Dec. 27, 1995

[51] Int. Cl.⁶ .................................................. C10M 135/04
[52] U.S. Cl. ........................................... 508/322; 508/323
[58] Field of Search ...................................... 508/322, 323

[56] References Cited

U.S. PATENT DOCUMENTS

| | | | |
|---|---|---|---|
| 3,673,090 | 6/1972 | Waldbillig et al. ...................... | 508/322 |
| 4,119,549 | 10/1978 | Davis ...................................... | 508/324 |
| 4,119,550 | 10/1978 | Davis et al. ............................. | 508/324 |
| 4,204,969 | 5/1980 | Papay et al. ............................. | 252/45 |
| 4,584,113 | 4/1986 | Walsh ...................................... | 508/322 |
| 5,338,468 | 8/1994 | Arvizzigno et al. .................... | 508/570 |

FOREIGN PATENT DOCUMENTS

| | | | |
|---|---|---|---|
| 0 201 197 A1 | 11/1986 | European Pat. Off. ...... | C07C 149/00 |
| WO92/00367 | 1/1992 | WIPO .......................... | C10M 105/72 |
| WO 92/03524 | 3/1992 | WIPO . | |
| WO92/03524 | 3/1992 | WIPO .......................... | C10M 135/04 |

*Primary Examiner*—Ellen M. McAvoy
*Attorney, Agent, or Firm*—John W. Ditsler

[57] ABSTRACT

This invention concerns a process for preparing a sulfurized olefin containing reduced amounts of thiones using a low molecular weight hydrocarbon to precipitate the thiones from the sulfurized olefin.

12 Claims, No Drawings

SULFURIZED OLEFIN COMPOSITION AND ITS METHOD OF PREPARATION

BACKGROUND OF THE INVENTION

This invention relates to a purified sulfurized olefin composition having low levels of thiones and to the method of its preparation.

Sulfurization of an olefin (i.e., contacting sulfur with an olefin) may produce impurities, including darkly colored by-products which are generally highly corrosive to copper. For example, sulfurization of isobutylene by direct reaction with sulfur forms a sulfurized isobutylene composition containing thione components, including 4-methyl-3H-1,2-dithiole-3-thione ("MDTT"). For many end uses, these by-products are undesirable because of their copper corrosivity and the dark color they impart. Reducing the concentration of these darkly colored components usually reduces the copper corrosiveness. Accordingly, a method of preparing sulfurized olefins that minimizes the formation of and/or decreases the presence of thiones without adversely affecting corrosivity is desirable.

Various methods have been suggested for preparing sulfurized olefins. For example, one method is described in U.S. Pat. No. 4,204,969 wherein a sulfurized olefin additive for lubricating oils is obtained by reacting sulfur monochloride with an aliphatic monoolefin to form an adduct, reacting the adduct with sulfur and sodium sulfide in an aqueous alkanol medium, and recovering the product by conventional methods, e.g., removing alkanol, water washing, and filtering. This method avoids the necessity of further treatment with an aqueous caustic. In the example presented, the patentee discloses first extracting a product with water to remove salts, separating the aqueous layer, and then extracting the remaining organic phase with water and hexane to further remove water soluble impurities, such as any remaining salts. The hexane is then distilled from the organic phase leaving the organic phase intact, which is then filtered to obtain a sulfurized olefin. However, U.S. Pat. No. 4,204,969 does not disclose that the hexane-containing organic layer can be treated for the removal of thiones. Furthermore, if a sulfurized olefin containing thiones were extracted with water as described in U.S. Pat. No. 4,204,969, the thiones would remain with the organic layer.

Another method is described in PCT/US91/05589 which discloses a halogen-free extreme-pressure antiwear additive obtained by reacting sulfur, an aqueous solution of an alkali metal salt of hydrosulfide or an alkaline earth metal salt of hydrosulfide or mixtures of an alkali metal salt and an alkaline earth metal salt of hydrosulfide, and one or more olefins. The reaction product obtained contains little or no dithiolethione. In an example, the patentees disclose decanting and filtering the organic product from the aqueous by-product after the reaction and state that additional organic product may be recovered by extracting the aqueous by-product with several portions of hexane, combining the extract, followed by evaporating the hexane. The extraction of the by-product is conducted in an aqueous environment for the purpose of recovering additional reaction product, not to reduce the level of thiones in the product.

Neither of the above methods suggests contacting a hydrocarbon with a sulfurized olefin composition in a non-aqueous medium. Therefore, in contrast to the methods described in U.S. Pat. No. 4,204,969 and PCT/US91/05589, disposal of aqueous sodium sulfide or aqueous chloride, which presents environmental concerns, is not required according to the present invention. In addition, an aqueous extraction according to either of the methods disclosed in these publications may recover additional sulfurized olefin rather than precipitate thione components in order to purify the sulfurized olefin produced.

This invention therefore provides a solution to the problems encountered in producing sulfurized olefin compositions containing thiones. Concurrently, this invention eliminates environmental concerns about the disposal of toxic aqueous solutions generated in an aqueous medium.

SUMMARY OF THE INVENTION

This invention relates to a process for preparing a sulfurized olefin containing low levels of thiones, which comprises:

(a) contacting sulfur with at least one olefin to form a sulfurized olefin composition, (b) removing at least a major amount of unreacted olefin from the sulfurized olefin composition formed in (a), (c) contacting the sulfurized olefin composition from (b) with a low molecular weight hydrocarbon to precipitate at least a major amount of the thione components, (d) removing the precipitated thione components from the product formed in (c), and (e) recovering the sulfurized olefin from the low molecular weight hydrocarbon.

In another embodiment, this invention relates to a purified sulfurized olefin as well as the specific sulfurized olefin produced by the process previously described.

DETAILED DESCRIPTION OF THE INVENTION

The first step of the process of this invention is olefin sulfurization. Essentially any appropriate sulfurization method can be used. For example, sulfurization of an olefin can be accomplished by directly combining sulfur with at least one olefin under temperature and pressure conditions suitable for forming the desired end product. Sulfurization of an olefin can also be accomplished by treating an olefin with sulfur and hydrogen sulfide. Preferably, sulfur is reacted directly with isobutylene to form sulfurized isobutylene. In this instance, the isobutylene is preferably added to the sulfur at a rate which controls the exothermic reaction and which maintains the pressure within the range discussed below.

Suitable olefins include alkenes such as propylene, isobutylene, and diisobutylene; terpenes such as alpha-pinene; Diels-Alder adducts such as bicycloheptene; fats such as lard; poly alpha-olefins such as poly-1-decene; and unsaturated fatty acids such as oleic acid. The olefin preferably is a C1 to C12 olefin, more preferably a C3 to C8 olefin. Most preferably, isobutylene is used. A single olefin or a mixture of more than one type of olefin can also be used.

If a mixture of olefins is used, preferably the mixture comprises a monoolefin in combination with a diolefin or polyolefin. For example, isobutylene and butadiene or dodecene and ethylidene-2-norbonene can be used in combination. The average carbon number of the olefin mixture is preferably within the range of 4 to 12 in order to maximize solubility and maintain a suitable pressure, as described below, during the reaction of olefin and sulfur and to provide a sulfurized olefin with good copper corrosivity, e.g., a rating of 2A or better in the ASTM D130 test for a formulated lubricant using 0.1 to 3% sulfur with or without additional copper passivators, e.g., tolyl triazole, thiadiazole, and phosphites.

In a mixture of monoolefin and diolefin or polyolefin, the molar ratio of monoolefin to diolefin or polyolefin depends on the reactivity and number of double bonds in the olefin monomers selected. For example, if isobutylene and butadiene are used, the molar ratio of isobutylene to butadiene preferably is in the range of about 50:1 to 9:1. If dodecene and ethylidene-2-norbonene are used, the molar ratio of dodecene to ethylidene-2-norbonene preferably is about 20:1 to 0.3:1. The average sulfur chain length in the sulfurized olefin prepared from a mixture of olefins is preferably about 1 to about 3.

When a mixture of monoolefin and diolefin or polyolefin is used, the monoolefin can be combined with sulfur and then, prior to completion of the reaction (i.e., when about 2 to about 50% by weight, based on the total weight of the reactants, of unreacted monoolefin remains) the diolefin or polyolefin can be added. Alternatively, if the diolefin or polyolefin is not too reactive (i.e., the reaction between the diolefin or polyolefin and sulfur does not automatically go to completion), the diolefin or polyolefin can be combined with sulfur and then, prior to completion of the reaction, i.e., when about 2 to about 50% by weight, based on the total weight of the reactants, of unreacted diolefin or polyolefin remains, the monoolefin can be added. Preferably, the monoolefin and diolefin or polyolefin are first combined together and then combined with sulfur.

After sulfurization, at least a major amount, preferable at least 75 wt. %, and more preferably substantially all unreacted olefin is removed, e.g., by stripping. The phrase "substantially all unreacted olefin" means either all unreacted olefin or all unreacted olefin with the exception of an amount of unreacted olefin which would not (i) result in a sulfurized olefin composition having a flash point which is too low, e.g., 100° C. or less, and/or (ii) cause the sulfurized composition to have an affinity for the thiones contained therein.

For the purpose of illustration in the following description, reference is made to the preferred sulfurization method where elemental sulfur is reacted directly with isobutylene.

The sulfur content of the sulfurized olefin composition can range from about 40 to about 55 weight %, based on the total weight of the sulfurized olefin composition. In other words, the molar ratio of sulfur to isobutylene in a direct reaction of elemental sulfur and isobutylene can range from about 1.17 to about 2.13. A sulfurized isobutylene with a higher sulfur content is generally preferable because higher sulfur products tend to have better extreme pressure properties—therefore, less product is needed in the finished oil. However, the higher the sulfur content of the sulfurized isobutylene, the greater the copper corrosivity. Thus, to maximize sulfur content, minimize corrosiveness, and maximize product yield, the more preferred amount of sulfur in the sulfurized olefin composition is 43 to 47 weight %, and the preferred range for the sulfur to isobutylene molar ratio is 1.32 to 1.55.

If desired, a catalyst may be used for the preparation of the sulfurized isobutylene. Suitable catalysts include, for example, phosphines such as tributylphosphines and amines such as tributylamine and polyisobutylene succinic anhydride polyamine dispersants.

The temperature during direct sulfurization of isobutylene generally ranges from about 120° to 180° C., preferably 140° to 180° C., more preferably 160° to 165° C. The particular temperature range is chosen in order to maximize the rate of the reaction while maintaining the amount of thione formation to below about 15 weight %, based on the weight of the sulfurized isobutylene.

A suitable pressure is one which makes the exothermic sulfurization reaction the easiest to control. For example, the pressure can be maintained within a range of from 150 to 1000 psig, preferably from 150 to 300 psig, and more preferably from 150 to 200 psig.

To minimize the initial concentration of the thiones, isobutylene is preferably added to molten sulfur at a temperature ranging from 160° to 165° C., preferably at a rate which controls the exothermic reaction and maintains the desired pressure. For example, in a five gallon autoclave containing about 8.3 kg of sulfur, a rate of about 5 to 25 grams/minute may be used. After the required amount of isobutylene has been added, the reaction is allowed to continue until the autogeneous pressure falls below about 75 psig. The autogeneous pressure generally falls to below about 75 psig after substantially all of the isobutylene has been reacted with the sulfur.

As noted above, after the sulfurization step is completed, it is preferred to remove the unreacted isobutylene, e.g., by stripping. Stripping can be accomplished by cooling the product to a temperature typically from 100°–110° C. (e.g. about 104° C.) and purging with nitrogen until the product has a flash point of at least 100° C.

The thione content of the sulfurized olefin composition can then be calculated by using a UV/VIS spectrophotometer to measure the light absorption of the sulfurized olefin samples. The calculation of the thione content uses the extinction coefficient disclosed in Mayer et al, J. Chromatog., 15, 153–167, (1964) for pure MDTT. The measurement captures thiones having an absorption at 415 nm in addition to MDTT. Therefore, the content (i.e., concentration) encompassing MDTT and these other thiones will be expressed throughout as "weight % MDTT equivalents."

Although a preferred method is described for the preparation of a sulfurized olefin, this invention is not limited to this preparation. Sulfurized olefin compositions prepared by convenient methods other than the direct reaction of elemental sulfur with isobutylene can also be used.

The next step of the process of this invention involves contacting the sulfurized olefin composition thus prepared with a hydrocarbon to precipitate at least a major portion, preferably at least 75 wt. %, of the thione components from the sulfurized olefin composition. Removal of precipitated thiones can also be effected by any convenient method, e.g., by decantation or filtration. The purified sulfurized olefin containing low levels of thione components can then be recovered after removing the hydrocarbon, e.g., by stripping. If desired, the hydrocarbon may be reused.

Suitable hydrocarbons have a low molecular weight, e.g., about 16 to about 170. Preferably, the hydrocarbon has a carbon number ranging from 1 to 12, more preferably from 2 to 5, and especially from 3 to 5. Propane is most preferred due to ease of handling in the liquid state and ease of removal from the sulfurized olefin composition, but pentane is also particularly effective. Hydrocarbons having a molecular weight that is too high, i.e., hydrocarbons having a carbon number above about 12, may be difficult to remove from the supernatant liquid after the precipitated thiones have been removed.

The low molecular weight hydrocarbon is preferably saturated. Although, unsaturated hydrocarbons and aromatics can be used, they are not preferred since thiones usually have a higher solubility in an unsaturated or aromatic medium. Linear and branched hydrocarbons are preferred, with linear hydrocarbons being most preferred.

The volume ratio of hydrocarbon to sulfurized olefin preferably ranges from about 0.5:1 to 10:1, more preferably from 1:1 to 5:1, and most preferably from 1:1 to 3:1.

The temperature during the contact of hydrocarbon with the sulfurized olefin composition can range from about −200° to about 150° C., preferably from −70° to 100° C., more preferably from −40° to 0° C. Contacting temperatures can be selected within these ranges by choosing a temperature at which the thiones are less soluble in order to achieve a more complete thione removal. Contacting temperatures can be achieved by any convenient method, e.g., auto-refrigeration. Auto-refrigeration evaporates some of the hydrocarbon, which in turn cools the solution by removing the latent heat of evaporation. For example, the solution of sulfurized olefin composition and low molecular weight hydrocarbon can be auto-refrigerated or the hydrocarbon can be auto-refrigerated and then contacted with the sulfurized olefin composition and additional auto-refrigeration can be performed if necessary. The evaporated hydrocarbon is usually condensed and may be recycled.

The sulfurized olefin composition is preferably contacted with propane at a temperature ranging from about −80° to about 25° C., preferably from −80° to 0° C., more preferably from −80° to −35° C., which is preferably achieved by auto-refrigeration. The sulfurized olefin composition is also conveniently extracted with pentane at a temperature ranging from about −80° to about 25° C., preferably from −80° to 0° C., more preferably from −80° to −35° C. Extraction with the lower molecular weight hydrocarbon within these temperature ranges will result in excellent removal of thiones.

If liquid hydrocarbons are used, the pressure during this step is one sufficient to maintain the hydrocarbon in the liquid state. For example, if the hydrocarbon is propane, the pressure necessary to keep propane as a liquid at ambient temperature can range from about 50 to about 150 psig. At the normal boiling point of propane, i.e., −42.1° C., the pressure required is about 0 psig (1 atmosphere). If auto-refrigeration is used to produce a low temperature during contact of the hydrocarbon with the sulfurized olefin composition, the pressure is reduced to evaporate the hydrocarbon and then maintained at a level necessary to keep the hydrocarbon as a liquid at that temperature.

The pressure used for hydrocarbons in the gaseous state is a vapor pressure above atmospheric, but depends on the particular hydrocarbon and contacting temperature selected. For example, ethane at −40° C. will require an elevated pressure of 110 psig (7.5 atm).

Following contacting the low molecular weight hydrocarbon with the sulfurized olefin composition, it is preferred to have a holding or a settling period sufficient to obtain a good separation—allow the MDTT to crystalize and separate from solution. This period should be at least 15 minutes, more preferably from 15 minutes to 2 hours. Prior to the settling period, the sulfurized olefin/hydrocarbon solution is preferably agitated, e.g., by gently stirring. The agitation can be performed for a period of from 1 hour to 8 hours, preferably from 1 hour to 2 hours.

At least a major amount, preferably at least 70 wt. %, typically from 50 to 98 wt. %, more preferably from 80 to 98 wt. %, of the total thione content present in the sulfurized olefin composition is precipitated. The precipitated thiones may then be separated from the sulfurized olefin/hydrocarbon solution, e.g., by decantation or filtering. The hydrocarbon is then removed from the sulfurized olefin/hydrocarbon solution, e.g., by stripping, distillation, or evaporation, and a purified sulfurized olefin containing low levels of thiones is recovered.

The steps of the process can be carried out in the same vessel or in different vessels.

This invention may be further understood from the following examples which are not intended to restrict the scope of the appended claims.

EXAMPLE 1

Peparation of Sulfurized Isobutylene

Two types of sulfurized isobutylene were prepared. The first type (SIB A) had a sulfur content of 53.5 wt. % and a thione content of 13.7 wt. % as MDTT equivalents. The second type (SIB B) had a sulfur content of 46.6 wt. % and a thione content of 10.8 wt. % as MDTT equivalents. Preparation of both types was similar and was conducted as follows:

Sulfur was first added to an autoclave and then heated to a temperature ranging from about 158° to 162° C. before the isobutylene was added. The target temperature for running the reaction was then set at 160° to 165° C. Throughout the preparation, the average pressure was substantially below 200 psig. The peak pressure during the preparation of SIB A was 215 psig, and the peak pressure during the preparation of SIB B was 210 psig. The reactions were run for about 17–26 hours.

EXAMPLE 2

Extraction of Sulfurized Isobutylene With Low Molecular Weight Hydrocarbons

A. Extraction With Liquid Hydrocarbons

SIB A was separately extracted with n-pentane, n-hexane, and n-heptane 15 separate experiments. The runs were conducted at a pressure of 0 psig (1 atm) and at a temperature of −78.5° C., with the exception of Run No. 7, which was conducted at room temperature (about 25° C.). The amount of sulfurized isobutylene, the type and amount of hydrocarbon, the ratio of hydrocarbon to sulfurized isobutylene, the reaction time, and an analysis of the recovered product are set forth in Table 1 below.

TABLE 1

| Run No. | SIB[1] (grams) | Hydrocarbon[2] Type | Grams | Ratio[3] | Time (hours) | Recovered Product[4] % Yield | % MDTT equivalents |
|---|---|---|---|---|---|---|---|
| 1 | 100.2 | C5 | 50.5 | 0.50 | 2 | — | 3.6 |
| 2 | 100.1 | C5 | 100.3 | 1.00 | 2 | 79.2 | 2.1 |
| 3 | 100.1 | C5 | 100.8 | 1.01 | ~18 | 77.8 | 3.4 |
| 4 | 100.0 | C5 | 200.4 | 2.00 | 2 | 73.1 | 1.1 |
| 5 | 100.0 | C5 | 300.1 | 3.00 | 2 | 78.8 | 1.2 |
| 6 | 100.0 | C5 | 400.1 | 4.00 | 2 | 78.7 | 1.2 |
| 7 | 106.1 | C5 | 500.6 | 4.72 | 2 | 101.2 | 10.2[5] |
| 8 | 100.2 | C6 | 50.3 | 0.50 | 2 | 70.9 | 4.9 |
| 9 | 100.1 | C6 | 100.3 | 1.00 | 2 | 77.9 | 3.2 |
| 10 | 100.0 | C6 | 100.5 | 1.05 | ~18 | 80.2 | 4.1 |
| 11 | 100.1 | C6 | 202.3 | 2.02 | 2 | 80.7 | 1.8 |
| 12 | 100.0 | C7 | 50.0 | 0.50 | 2 | 77.5 | 5.6 |
| 13 | 100.0 | C7 | 100.2 | 1.00 | 2 | 80.0 | 3.2 |
| 14 | 100.0 | C7 | 104.0 | 1.04 | ~18 | 92.4 | 3.6 |
| 15 | 100.1 | C7 | 200.8 | 2.01 | 2 | 80.5 | 1.8 |

TABLE 1-continued

| Run No. | SIB[1] (grams) | Hydrocarbon[2] Type | Grams | Ratio[3] | Time (hours) | % Yield | Recovered Product[4] % MDTT equivalents |
|---|---|---|---|---|---|---|---|

[1]SIB (sulfurized isobutylene) having 53.5 wt. % sulfur and a thione content of 13.7 wt. % as MDTT equivalents.
[2]Hydrocarbon refers to hydrocarbons which are normally liquid at ambient conditions. C5 refers to n-pentane, C6 refers to n-hexane, and C7 refers to n-heptane.
[3]Ratio refers to grams of hydrocarbon per gram of SIB.
[4]Removal of all traces of the C5 to C7 hydrocarbons is more difficult. Therefore, measured product yield may be slightly higher than actual yield.
[5]Experiment run at room temperature.

In general, extraction with a C5 hydrocarbon removes more thiones than extraction with a C6 or C7 hydrocarbon under the same conditions. Also, higher ratios of hydrocarbon to SIB result in better removal of thiones. This effect appears to plateau as the ratio increases. For example, as shown in Table 1 for pentane, the percent of MDTT equivalents levels out at about 1.1 to 1.2% as the ratio of hydrocarbon to SIB reaches about 2.0.

B. Extraction With Pentane

SIB B was extracted with pentane in 9 separate experiments. The tests were conducted at a pressure of 0 psig (1 atm) and a temperature ranging from about −18° to −19° C. as indicated in Table 2. The runs were conducted in a manner similar to that described above. In the first five runs (1 to 5), after the pentane and sulfurized isobutylene were contacted, the mixture was allowed to settle for about two hours. In the last four runs (6 to 9), the pentane/sulfurized isobutylene solution was agitated for one hour prior to a settling period of two hours at the temperature of the cold bath, i.e., −18° to −19° C. The extractant layer was then decanted, stripped of pentane, and analyzed for % MDTT equivalents. The amount of sulfurized isobutylene, the volume-to-volume ratio of pentane to sulfurized isobutylene, and an analysis of the extractant are set forth in Table 2 below.

C. Extraction With Propane and Butane at −78.5° C.

SIB A was separately extracted with propane and n-butane in 8 individual runs. The runs were conducted at a temperature of −78.5° C. and a pressure of 0 psig (1 atm). The amount of sulfurized isobutylene, the type and amount of hydrocarbon, the ratio of hydrocarbon to sulfurized isobutylene, the reaction time, and the recovered product are set forth in Table 3 below.

TABLE 3

| Run No. | SIB[1] (grams) | Hydrocarbon[2] Type | Grams | Ratio[3] | Time (hours) | % Yield | Recovered Product % MDTT eqivalents |
|---|---|---|---|---|---|---|---|
| 16 | 25.7 | C3 | 43.5 | 1.69 | 2 | 70.0 | 1.0 |
| 17 | 25.1 | C3 | 51.8 | 2.06 | 2 | 72.3 | 0.7 |
| 18 | 20.4 | C3 | 59.2 | 2.90 | 2 | 75.8 | 0.7 |
| 19 | 15.3 | C3 | 53.2 | 3.48 | 2 | 74.6 | 0.5 |
| 20 | 25.8 | C4 | 44.0 | 1.71 | 1 | 77.5 | 1.8 |
| 21 | 25.2 | C4 | 51.6 | 2.05 | 1 | 72.2 | 1.3 |
| 22 | 25.1 | C4 | 57.6 | 2.29 | 2 | — | 0.9 |
| 23 | 15.2 | C4 | 48.7 | 3.20 | 2 | 75.7 | 0.6 |

[1]SIB having 53.5 wt. % sulfur and a thione content of 13.7 wt. % as MDTT equivalents.
[2]Hydrocarbon refers to hydrocarbons which are normally gaseous at ambient conditions. C3 is propane and C4 is n-butane.
[3]Ratio refers to grams of hydrocarbon per gram of SIB.

Extraction with C3 and C4 hydrocarbons at dry ice temparature, i.e., −78.5° C., as shown in Table 3, illustrates the preference for lower molecular weight hydrocarbons. At the same extraction conditions, a C3 hydrocarbon is generally better than a C4 hydrocarbon in removing thiones. The results also illustrate that the higher the ratio of hydrocarbon to SIB, the lower the concentration of remaining thiones.

D. Extraction With Propane at −38° C.

SIB A was extracted with propane in 3 separate runs, and SIB B was extracted with propane in 7 separate runs. The runs were conducted at a temperature of −38° C. and a

TABLE 2

| Run No. | Temp. (°C.) | SIB[1] (grams) | Pentane (grams) | Pentane (ml) | Ratio[2] | Extractant (grams) | % Yield | % MDTT equivalents |
|---|---|---|---|---|---|---|---|---|
| 1 | −18 | 108.0 | 62.6 | 100 | 1.0 | 92.5 | 85.6 | 4.79 |
| 2 | −19 | 108.0 | 125.4 | 200 | 2.0 | 97.0 | 89.8 | 3.45 |
| 3 | −18 | 108.0 | 187.8 | 300 | 3.0 | 88.3 | 81.8 | 2.91 |
| 4 | −18 | 108.0 | 250.8 | 401 | 4.0 | 94.0 | 87.0 | 3.33 |
| 5 | −18 | 108.0 | 313.9 | 501 | 5.0 | 94.5 | 87.5 | 3.18 |
| 6 | −18 | 108.0 | 125.8 | 201 | 2.0 | 86.0 | 79.6 | 2.93 |
| 7 | −18 | 108.0 | 187.6 | 300 | 3.0 | 93.0 | 86.1 | 2.68 |
| 8 | −18 | 108.2 | 250.9 | 401 | 4.0 | 92.3 | 85.3 | 2.73 |
| 9 | −18 | 108.1 | 313.9 | 501 | 5.0 | 92.1 | 85.2 | 2.88 |

[1]SIB having 46.6% sulfur and a thione content of 10.8% as MDTT equivalents. The volume of SIB used was 100 ml.
[2]Ratio refers to volume of hydrocarbon per volume of SIB.

As shown in Table 2, a preferred embodiment of this invention is to extract with pentane at about −18° C. using agitation for one hour prior to a two hour settling period. The additional hour of agitation further lowers the amount of MDTT equivalents present in the extractant.

pressure of 0 psig (1 atm). The type and amount of sulfurized isobutylene, the amount of propane, the ratio of propane to sulfurized isobutylene, the reaction time, and the recovered product are set forth in Table 4 below.

TABLE 4

| Run No. | SIB Type[3] | SIB Grams | Propane | Ratio[1] | Time | % Yield | Recovered Product[2] % MDTT equivalents |
|---|---|---|---|---|---|---|---|
| 24 | H | 100.0 | 293 | 2.93 | 0.58 | 72.2 | 1.06 |
| 25 | H | 100.3 | 293 | 2.92 | 0.42 | 74.1 | 1.15 |
| 26 | H | 100.3 | 293 | 2.92 | 1.00 | 73.9 | 1.23 |
| 27 | L | 101.8 | 500 | 4.92 | 1.42 | 83.0 | 1.41 |
| 28 | L | 101.6 | 293 | 2.88 | 0.92 | 83.0 | 1.46 |
| 29 | L | 266.0 | 585 | 2.20 | 1.25 | — | 1.91 |
| 30 | L | 268.1 | 585 | 2.18 | 1.17 | 79.2 | 1.68 |
| 31 | L | 269.2 | 585 | 2.17 | 1.25 | 78.2 | 1.70 |
| 32 | L | 269.7 | 585 | 2.17 | 1.25 | 80.5 | 1.94 |
| 33 | L | 272.1 | 585 | 2.15 | 1.25 | 85.3 | 2.12 |

[1] Ratio refers to grams of propane per gram of SIB.
[2] Experimentation revealed that propane is not difficult to remove. Therefore, yield should reflect only the purified product.
[3] H represents SIB A; L represents SIB B.

Propane extraction at the normal boiling point of about −40° C. is another embodiment of the present invention. The results of Run Nos. 27 to 33 illustrate that extraction of a SIB sample containing 46.6 wt. % sulfur is more preferred than extraction of a SIB sample containing 53.5 wt. % since and even higher yield of recovered product is obtained at 46.6 wt. % sulfur.

What is claimed is:

1. A process for preparing a sulfurized olefin containing low levels of thiones, which comprises:
   (a) contacting sulfur with at least one olefin to form a sulfurized olefin composition,
   (b) removing at least a major amount of unreacted olefin from the sulfurized olefin composition formed in (a),
   (c) contacting the sulfurized olefin composition from (b) with a low molecular weight hydrocarbon to precipitate at least a major amount of the thione components,
   (d) removing the precipitated thione components from the product formed in (c), and
   (e) recovering the sulfurized olefin from the low molecular weight hydrocarbon.

2. The process of claim 1, wherein at least one olefin has a carbon number ranging from one to twelve.

3. The process of claim 1, wherein at least one olefin is isobutylene.

4. The process of claim 1, wherein at least one olefin comprises a monoolefin in combination with a diolefin or polyolefin.

5. The process of claim 1, wherein (c) occurs at a temperature ranging from −200° to 150° C.

6. The process of claim 1, wherein the low molecular weight hydrocarbon has a carbon number ranging from one to twelve.

7. The process of claim 3, wherein the low molecular weight hydrocarbon is a saturated $C_3$ to $C_5$ hydrocarbon.

8. A process for preparing a sulfurized isobutylene containing low levels of thiones, which comprises:
   (a) contacting sulfur with isobutylene at a temperature ranging from about 140° to about 180° C. while maintaining pressure below about 210 psig to form a sulfurized isobutylene composition,
   (b) removing at least a major amount of unreacted isobutylene from the sulfurized isobutylene composition formed in (a),
   (c) extracting the sulfurized isobutylene composition with a saturated C3 to C5 hydrocarbon at a temperature between −80° and −35° C. for a period of time sufficent to precipitate at least a major amount of the thione components,
   (d) removing the precipitated thione components by decantation or filtration,
   (e) removing the propane, and
   (f) recovering the sulfurized isobutylene.

9. The process of claim 8, wherein the hydrocarbon used in (c) is propane or pentane.

10. The process of claim 8, wherein the temperature in (c) is achieved by auto-refrigeration.

11. The process of claim 1 wherein at least 70 wt. % of the total thione content present in the sulfurized olefin composition is precipitated in (c).

12. The process of claim 8 wherein at from 80 to 98 wt. % of the total thione content present in the sulfur isobutylene composition is precipitated in (c).

* * * * *